(12) United States Patent
Tanikawa et al.

(10) Patent No.: US 11,980,491 B2
(45) Date of Patent: May 14, 2024

(54) AUTOMATIC RECOGNITION METHOD FOR MEASUREMENT POINT IN CEPHALO IMAGE

(71) Applicant: OSAKA UNIVERSITY, Suita (JP)

(72) Inventors: Chihiro Tanikawa, Suita (JP); Chonho Lee, Suita (JP)

(73) Assignee: OSAKA UNIVERSITY, Suita (JP)

( * ) Notice: Subject to any disclaimer, the term of this patent is extended or adjusted under 35 U.S.C. 154(b) by 503 days.

(21) Appl. No.: 17/280,698

(22) PCT Filed: Sep. 24, 2019

(86) PCT No.: PCT/JP2019/037260
§ 371 (c)(1),
(2) Date: Mar. 26, 2021

(87) PCT Pub. No.: WO2020/067005
PCT Pub. Date: Apr. 2, 2020

(65) Prior Publication Data
US 2022/0005222 A1 Jan. 6, 2022

(30) Foreign Application Priority Data

Sep. 27, 2018 (JP) .................................. 2018-181619

(51) Int. Cl.
*A61B 6/50* (2024.01)
*A61C 7/00* (2006.01)
(Continued)

(52) U.S. Cl.
CPC .............. *A61B 6/501* (2013.01); *A61C 7/002* (2013.01); *G06N 20/00* (2019.01); *G06T 7/74* (2017.01);
(Continued)

(58) Field of Classification Search
CPC ........... A61B 6/501; A61B 6/14; A61C 7/002; G06N 20/00; G06T 7/74;
(Continued)

(56) References Cited

U.S. PATENT DOCUMENTS 9,336,302 B1 * 5/2016 Swamy ............... G06F 16/2465
9,990,712 B2 * 6/2018 Gazit ..................... A61B 6/032
(Continued)

FOREIGN PATENT DOCUMENTS

CN 104598909 A 5/2015
JP 2004-105604 A 4/2004
(Continued)

OTHER PUBLICATIONS

Fully automated quantitative cephalometry using convolutional neural networks Sercan Ö. Ank,a,† Bulat Ibragimov,b,*,† and Lei Xingb (Year: 2017).*

(Continued)

*Primary Examiner* — Dhaval V Patel
(74) *Attorney, Agent, or Firm* — Birch, Stewart, Kolasch & Birch, LLP (57) ABSTRACT

A technique for automating the identifying of a measurement point in cephalometric image analysis is provided. An automatic measurement point recognition method includes a step of detecting, from a cephalometric image 14 acquired from a subject, a plurality of peripheral partial regions 31, 32, 33, 34 for recognizing a target feature point, a step of estimating a candidate position of the feature point in each of the peripheral partial regions 31, 32, 33, 34 by the application of a regression CNN model 10, and a step of determining the position of the feature point in the cephalometric image 14 based on the distribution of the candidate positions estimated. In the step of detecting, for example, the
(Continued)

peripheral partial region 32, a classification CNN model 13 trained with a control image 52 is applied.

12 Claims, 10 Drawing Sheets

(51) Int. Cl.
| | |
|---|---|
| *G06N 20/00* | (2019.01) |
| *G06T 7/73* | (2017.01) |
| *G06V 10/75* | (2022.01) |
| *G06V 10/764* | (2022.01) |
| *G06V 10/82* | (2022.01) |

(52) U.S. Cl.
CPC .......... *G06V 10/751* (2022.01); *G06V 10/764* (2022.01); *G06V 10/82* (2022.01); *G06T 2207/10116* (2013.01); *G06T 2207/20076* (2013.01); *G06T 2207/20081* (2013.01); *G06T 2207/20084* (2013.01); *G06T 2207/30036* (2013.01)

(58) Field of Classification Search
CPC .......... G06T 2207/10116; G06T 2207/20076; G06T 2207/20081; G06T 2207/20084; G06T 2207/30036; G06T 7/70; G06V 10/751; G06V 10/764; G06V 10/82; G06V 2201/03
See application file for complete search history.

(56) References Cited

U.S. PATENT DOCUMENTS

| | | | |
|---|---|---|---|
| 10,990,849 B2* | 4/2021 | Xiao | ................ G06F 16/90335 |
| 11,205,103 B2* | 12/2021 | Zhang | ................... G06N 3/045 |
| 2010/0254582 A1 | 10/2010 | Liu et al. | |
| 2011/0123081 A1 | 5/2011 | Sebok et al. | |
| 2015/0186748 A1* | 7/2015 | Cootes | .............. G06F 18/24323 |
| | | | 382/201 |
| 2018/0061054 A1 | 3/2018 | Abraham et al. | |
| 2018/0311013 A1 | 11/2018 | Tanikawa et al. | |

FOREIGN PATENT DOCUMENTS

| | | |
|---|---|---|
| JP | 2005-13363 A | 1/2005 |
| WO | WO 2017/069231 A1 | 4/2017 |

OTHER PUBLICATIONS

International Search Report (PCT/ISA/210) issued in PCT/JP2019/037260, dated Dec. 17, 2019.
Ricketts, "The Value of Cephalometrics and Computerized Technology," Angle Orthod., vol. 42, No. 3, Jul. 1972, pp. 179-199.
Wang et al., "Evaluation and Comparison of Anatomical Landmark Detection Methods for Cephalometric X-Ray Images: A Grand Challenge," IEEE Transactions on Medical Imaging, vol. 34, No. 9, Sep. 2015, pp. 1890-1900.
Written Opinion of the International Searching Authority (PCT/ISA/237) issued in PCT/JP2019/037260, dated Dec. 17, 2019.
Chonho Lee et al.,"Deep Learning based Cephalometric Landmark Identification using Landmark-dependent Multi-scale Patches", pp. 1-5, Jun. 7, 2019.
Office Action and Search Report issued in Chinese Patent Application No. 201980063247.9 on Mar. 9, 2024, with English translation.

* cited by examiner

AUTOMATIC RECOGNITION METHOD FOR MEASUREMENT POINT IN CEPHALO IMAGE

TECHNICAL FIELD

The present invention relates to a cephalometric image analysis technique, and more particularly relates to a technique of automating the identification of anatomical feature points (measurement points) on a cephalometric image by a deep learning processing with AI (artificial intelligence).

BACKGROUND ART

Morphological analysis of a craniomaxillofacial region based on an X-ray standard image (hereinafter, referred to as "cephalometric image") is one of the important analysis techniques in orthodontic diagnosis. This cephalometric image analysis has roughly the following three steps (see FIG. 1). First, in the first step, a plurality of measurement points is identified based on anatomical features in a cephalometric image acquired from a patient. Next, in the second step, geometric relationships (such as distances and angles) between some of the identified measurement points that are necessary for the analysis are measured. In the final step, the measured values thus obtained are compared with reference values obtained from a population whose age, sex, etc. match those of the patient who is the subject and who have normal occlusion, and thereby the degree of bias of the patient is assessed.

The analytical processing in the second and third steps described above deals with only pixel coordinate values of positions of the identified measurement points. Thus, this processing is feasible by relatively simple computation and is already highly automated (see, for example, Non Patent Literature 1). However, the identifying of measurement points in the first step described above has not been fully automated and exclusively relies on doctor's visual judgment because the work requires sophisticated expertise and experiences of a dentist. For example, the measurement in the morphological analysis of a craniomaxillofacial region involves as many as at least twenty feature points. Moreover, features on soft tissues have to be interpreted while adjusting the contrast of the radiograph. These and other facts place a significant burden on dentists by forcing them to concentrate and make judgements for long periods of time in order to accurately identify the positions of all measurement points (feature points).

Regarding the automatic recognition of a measurement point on a cephalometric image, for example, methods have been proposed so far which make the recognition by using knowledge information or which identify a measurement point by pattern recognition. Unfortunately, these methods have not been clinically applied for reasons such as because the mathematical model created with a software requires a huge number of calculation steps and also requires a supercomputer-level processing capacity.

In recent years, the enhancement in the processing capacity of computers and the birth of advanced analysis engines through the development of sophisticated algorithms have led to movements to bring an image recognition technique based on machine learning, especially deep learning, into practical use in various fields. For example, Patent Literature 1 discloses that a process identifying positions of anatomical landmarks on a cephalometric image is performed by an algorithm using CNN (convolutional neural network).

CITATION LIST

Patent Literature

Patent Literature 1: U.S. Patent Application Publication No. 2018/0061054
Non Patent Literature 1: Ricketts, R. M. (1972), The value of cephalometrics and computerized technology. Angle Orthod., 42, 179-99.

SUMMARY OF INVENTION

Technical Problem

As mentioned above, the identifying positions of a measurement point in cephalometric image analysis is currently made based on sophisticated expertise and experiences of specialists such as doctors. The development of high-spec special hardware has been considered necessary for the automation of the identifying positions of a measurement point on a practical level.

In view of these circumstances, an object of the present invention is to provide a technique for automating the identifying of a measurement point in cephalometric image analysis without using special hardware.

Solution to Problem

To solve the problems discussed above, an aspect of the present invention resides in an automatic measurement point recognition method wherein a measurement point in a cephalometric image is automatically recognized with an arithmetic processor, the method including a step of detecting, from a cephalometric image acquired from a subject, a plurality of peripheral partial regions different from one another that have been predetermined with respect to a feature point of interest, a step of estimating a candidate position of the feature point in each of the peripheral partial regions using a deep learning model trained to learn positions of the feature point in peripheral partial regions, and a step of determining a most likely estimated position of the feature point in the cephalometric image based on the distribution of the candidate positions estimated, and determining that the most likely estimated position is the position of the measurement point.

Preferably, the peripheral partial regions have different image sizes from one another, and in the step of detecting the peripheral partial regions, the peripheral partial regions are each detected by comparison with a control image having the same size as the peripheral partial region.

In the step of determining the position of the feature point, it is preferable that the candidate position closest to the peak top of the distribution density of the candidate positions be determined as the most likely estimated position of the feature point.

In the step of determining the position of the feature point, the position of the peak top of the distribution density of the candidate positions may be determined as the most likely estimated position of the feature point.

When the distribution density of the candidate positions shows at least two or more peaks and when any two candidate positions estimated as most likely positions from the tops of the respective peaks are distant from each other by a predetermined threshold value or a greater distance, the step of determining the position of the feature point preferably includes a processing that determines that the two candidate positions are separate measurement points with respect to the feature point.

Another aspect of the present invention resides in an automatic measurement point recognition system including an arithmetic processor capable of automatically recognizing a measurement point in a cephalometric image, and a database, wherein the database stores information of a plurality of control images showing peripheral partial regions different from one another that have been predetermined with respect to a feature point of interest, and a deep learning model trained to learn positions of the feature point in the peripheral partial regions, and the arithmetic processor includes a peripheral partial region detecting unit that detects, from a cephalometric image acquired from a subject, a plurality of peripheral partial regions that match the control images, a feature point position estimating unit that estimates a candidate position of the feature point in each of the peripheral partial regions using the deep learning model, and a most likely position determining unit that determines a most likely estimated position of the feature point in the cephalometric image based on the distribution of the candidate positions estimated, and determines that the most likely estimated position is the position of the measurement point.

Preferably, the peripheral partial regions have different image sizes from one another, and the peripheral partial region detecting unit detects each of the peripheral partial regions by comparison with the control image having the same size as the peripheral partial region.

The most likely position determining unit is preferably configured to determine that the candidate position closest to the peak top of the distribution density of the candidate positions is the most likely estimated position of the feature point.

The most likely position determining unit may be configured to determine that the position of the peak top of the distribution density of the candidate positions is the most likely estimated position of the feature point.

When the distribution density of the candidate positions shows at least two or more peaks and when any two candidate positions estimated as most likely positions from the tops of the respective peaks are distant from each other by a predetermined threshold value or a greater distance, the most likely position determining unit preferably determines that the two candidate positions are separate measurement points with respect to the feature point.

Advantageous Effects of Invention

The present invention provides an algorithm or a system capable of recognizing an anatomical feature point in cephalometric image analysis with high accuracy and less load. As a result, the identifying of a measurement point in a cephalometric image may be automated without using high-spec special hardware.

DESCRIPTION OF EMBODIMENTS

Figure 1:
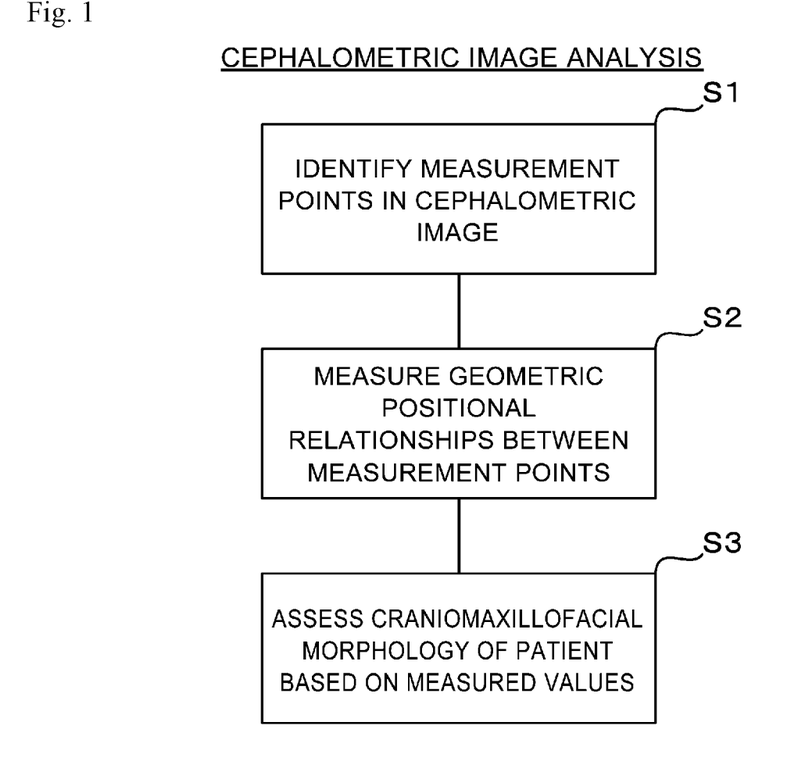
FIG. 1 is a flowchart illustrating the outline of cephalometric image analysis performed in orthodontic diagnosis.

In orthodontic diagnosis, cephalometric image analysis is one of the important techniques for analyzing the morphology of a craniomaxillofacial region of a patient. As illustrated in FIG. 1, this cephalometric image analysis has roughly three steps. First, a plurality of measurement points is identified based on anatomical features in a cephalometric image acquired from a patient (Step S1). Next, geometric positional relationships (such as distances and angles) between some of the identified measurement points that are necessary for the analysis are measured (Step S2). The measured geometric values thus obtained are compared with reference values obtained from a population whose age, sex, etc. match those of the patient who is the subject and who have normal occlusion, and thereby the degree of bias of the patient is assessed (Step S3). The present invention pertains to a method of automatically identifying or recognizing a measurement point (that is, an anatomical feature point) in Step S1 through a deep learning processing by a computer. Hereinbelow, specific embodiments of the method will be described in detail with reference to the drawings.

A cephalometric image is acquired by taking an X-ray image of a lateral head of a subject who is a patient under a certain standard. Specifically, the distance between the center of the subject and the focal point of the X-ray tube, and the distance between the subject and the film surface are each kept constant, and the main X-ray is held at a position where the main X-ray penetrates the central axis of both ear rods (in the case of the side view position). The X-ray standard image obtained in this manner allows for over-time comparison and consideration.

Figure 2:
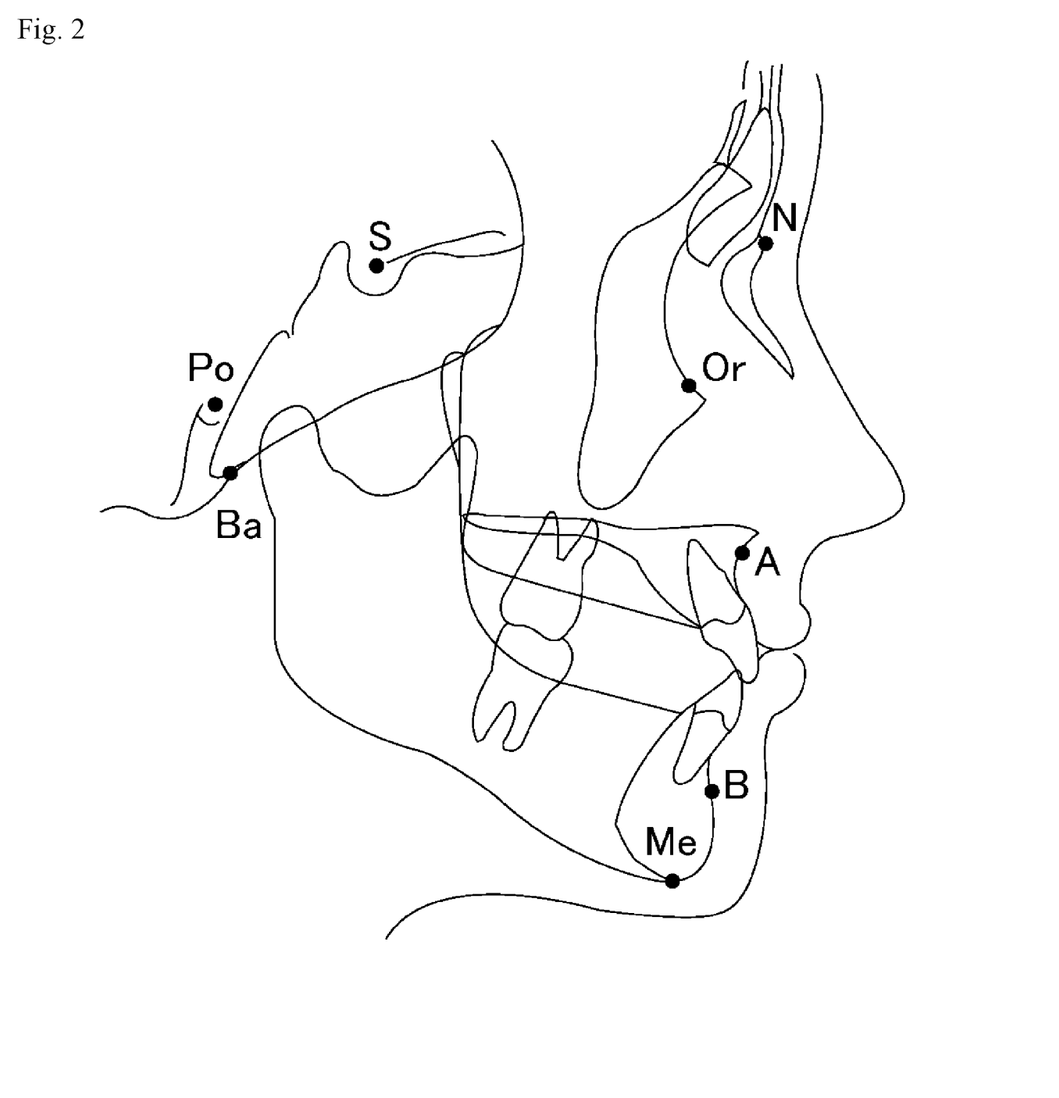
FIG. 2 is a view illustrating typical anatomical feature points read from a lateral head image.

FIG. 2 shows some typical anatomical feature points (landmarks) that can be read from a lateral head image. By measuring, for example, the lengths and angles of lines connecting these feature points, the sizes and misalignment of the maxilla and mandible, the shape of the jaws, the inclination angle of the teeth, the balance of the mouth, etc. can be quantitatively evaluated. Further, changes before and after a surgery can be observed.

According to the present embodiment, an anatomical feature point that is a measurement point in cephalometric image analysis is identified by an image recognition processing performed by an arithmetic processor using a deep learning model. The deep learning model that is used may be, for example, a regression arithmetic processing using a convolutional neural network (CNN) model. Here, the outline of automatic recognition of a feature point using a regression convolutional neural network model (hereinafter, written as "regression CNN model") will be described with reference to FIGS. 3 to 5.

Figure 3:
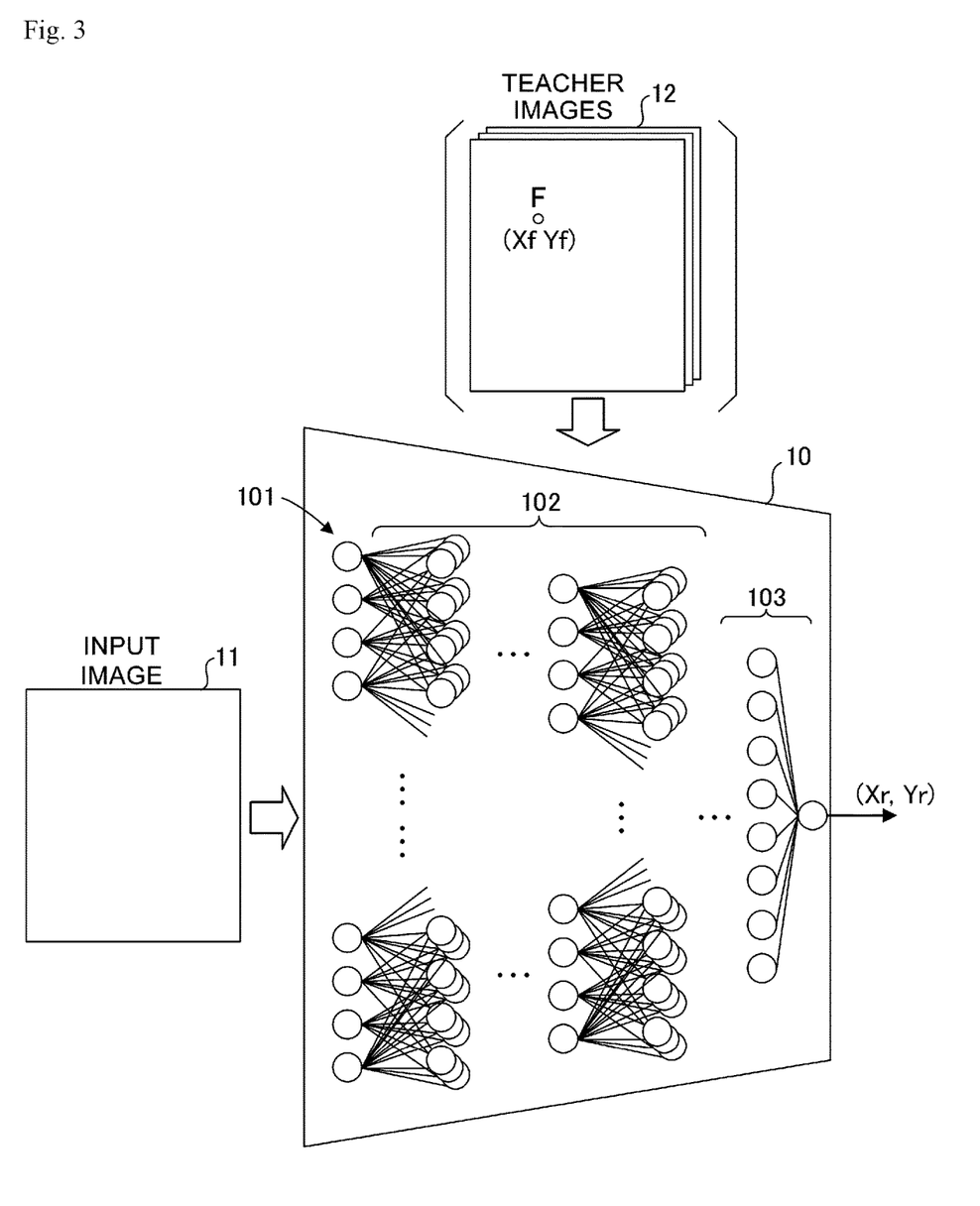
FIG. 3 is a view illustrating a system that automatically recognizes a feature point by applying a regression CNN model to an input image.

A regression CNN model 10 has been trained with a large amount of teacher images 12 in which the position (Xf, Yf) of a certain feature point F is already known. The teacher images 12 may show the whole of cephalometric images or may show regions clipped so as to include the feature point F. In the present embodiment, basically, the position (Xr, Yr) of the feature point F in an input image 11 is estimated by a regression arithmetic processing using the teacher images 12 that have been learned.

The regression CNN model 10 has at least an input layer 101, hidden layers (deep learning layers) 102 and an output layer 103. First, the image data of the input image 11 is captured as such into the input layer 101. In more detail, pixel values of the input image 11, specifically, the gray scales of the X-ray image converted to "0" to "1" are input into the corresponding neurons of the input layer 101.

In the hidden layers 102, patterns of various features constituting the input image 11 are extracted. The neurons in the columns of the hidden layers 102 illustrated in FIG. 3 each calculate the linear sum of weighted inputs, and thereby play a role of determining respective feature patterns different from one another. By adjusting the weighting coefficient for each of the neurons, the neurons learn which feature they should evaluate. These neurons compare the sequence data input from the previous layer with the sequence data of the feature that have been learned in advance, and pass values indicating the degree of mutual matching (the degree of similarity) to the column of neurons in the next layer. The results determined by the neurons are preferably activated by, for example, ReLU (Rectified Linear Units) or the sigmoid function to reduce the gradient loss due to the increase of deep learning layers.

If the extraction of features by the deep learning layers is performed collectively over the entire image, the number of synapses that is required to transmit information to one neuron is as many as the resolution (the number of pixels) of the input image. Consequently, the amount of data that is processed is extremely increased. To solve this problem, the present embodiment adopts CNN (convolutional neural network) for the feature extraction. When the deep learning model is CNN, as illustrated in, for example, FIGS. 4 and 5, the image information in the input layer 101 is subdivided into a plurality of pieces 101A, 101B, 101C, 101D which each correspond to a small region, and the neurons 1021, 1022, . . . of the hidden layer 102 determine the degree of matching of the feature with respect to each of these pieces 101A, 101B, 101C, 101D. By determining the degree of matching with respect to all the pieces of the primary sequence data (the image data in the case of the first stage), the size of the secondary sequence data (intermediate data) may be reduced.

Figure 4:
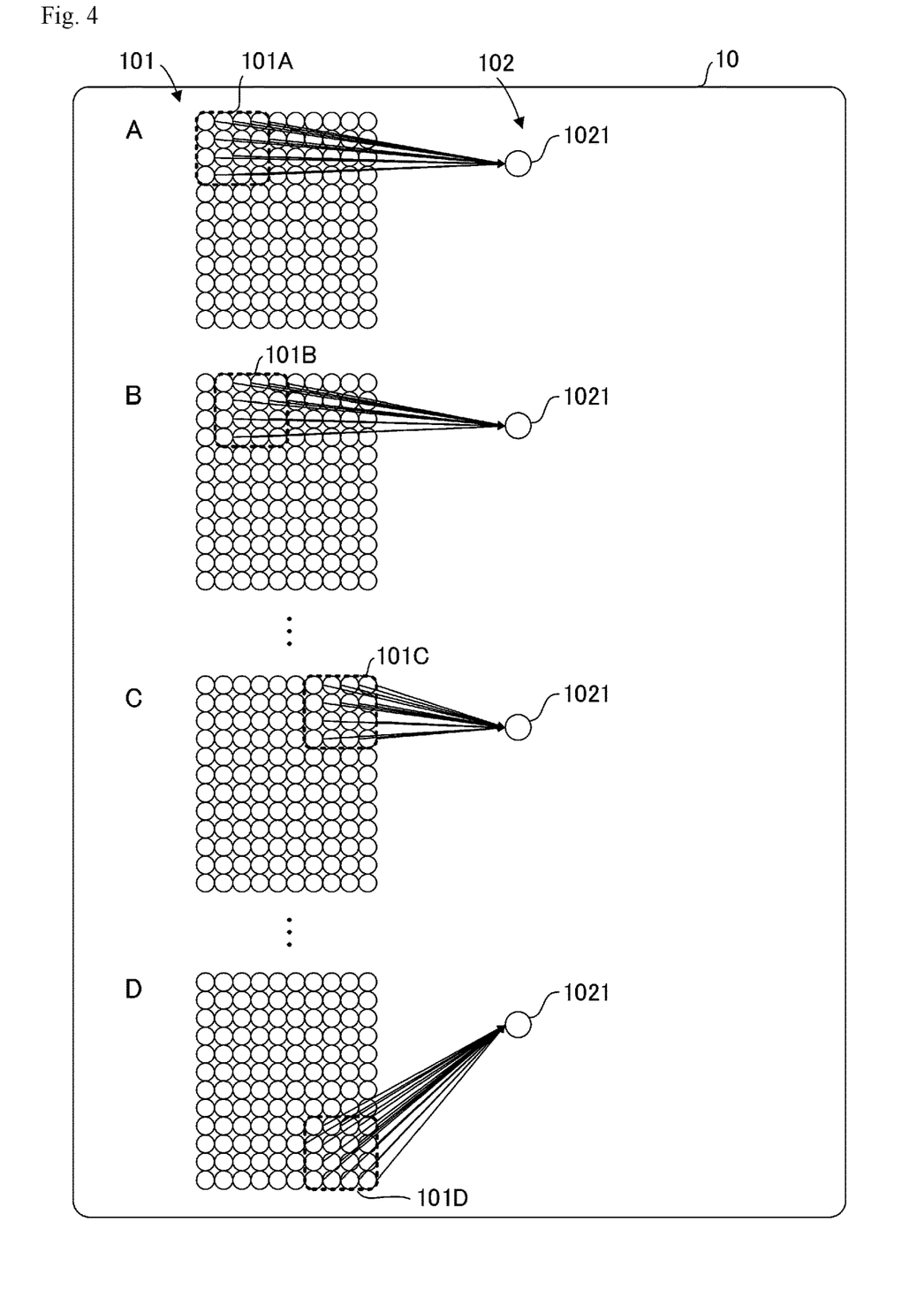
FIG. 4 is a view further illustrating a system that automatically recognizes a feature point using a regression CNN model.
Figure 5:
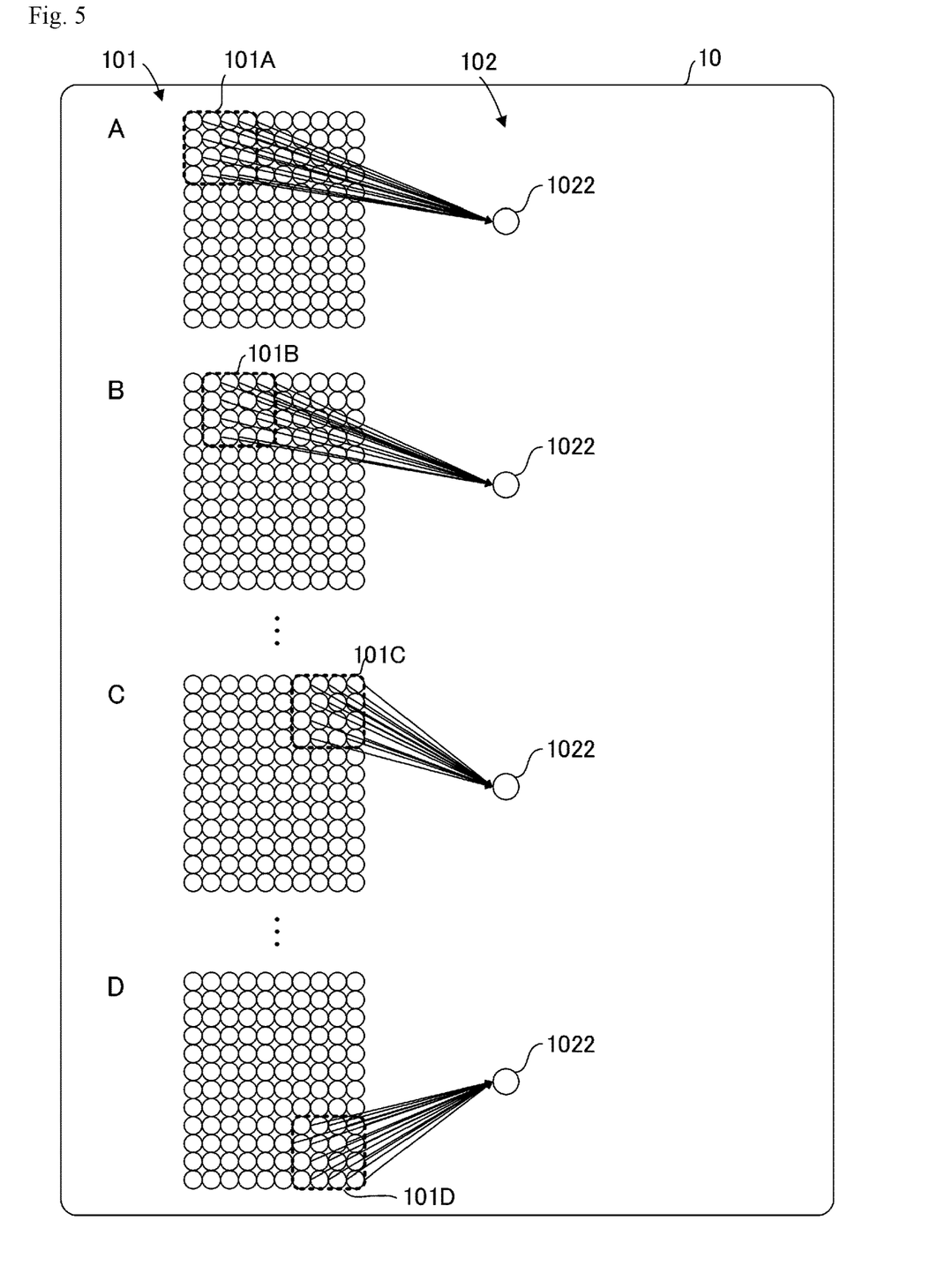
FIG. 5 is a view further illustrating a system that automatically recognizes a feature point using a regression CNN model.

In the hidden layers 102 that are deep learning layers, the above processing that determines the degree of matching is sequentially repeated in a multi-layered manner, and finally gives small-sized feature extraction data that emphasizes the consistency with the teacher images 12. In each of the deep learning layers, a pooling processing that reduces the size of the intermediate data may be appropriately performed to reduce the load of information processing on the computer.

The data (the feature extraction data sequence) that include features extracted from the piece patterns and are output from the hidden layers 102 are finally passed to the output layer 103. In the output layer 103, the weighting coefficient for the neural network has been tuned so that the error will be minimum between the estimated position of the feature point F obtained from feature extraction data of a given input image and the position (Xf, Yf) of the feature point F obtained from the feature extraction data of the teacher images 12. By executing a regression arithmetic processing in the output layer 103 on the feature extraction data extracted from the input image 11, the estimated position (Xr, Yr) of the feature point F in the input image 11 may be obtained.

In the regression arithmetic processing described above, the position of a feature point may be generally estimated more accurately with increasing area of an input image 11 (that is, with increasing number of pixels). If, however, the regression arithmetic processing is performed over the entirety of a cephalometric image at once, the amount of information processed by the computer is extremely increased and the calculation time is extended. Thus, the system in the present embodiment adopts a novel algorithm described below in order to attain a high location estimation accuracy and to reduce the load of the arithmetic processing in the automatic recognition of a feature point.

Figure 6:
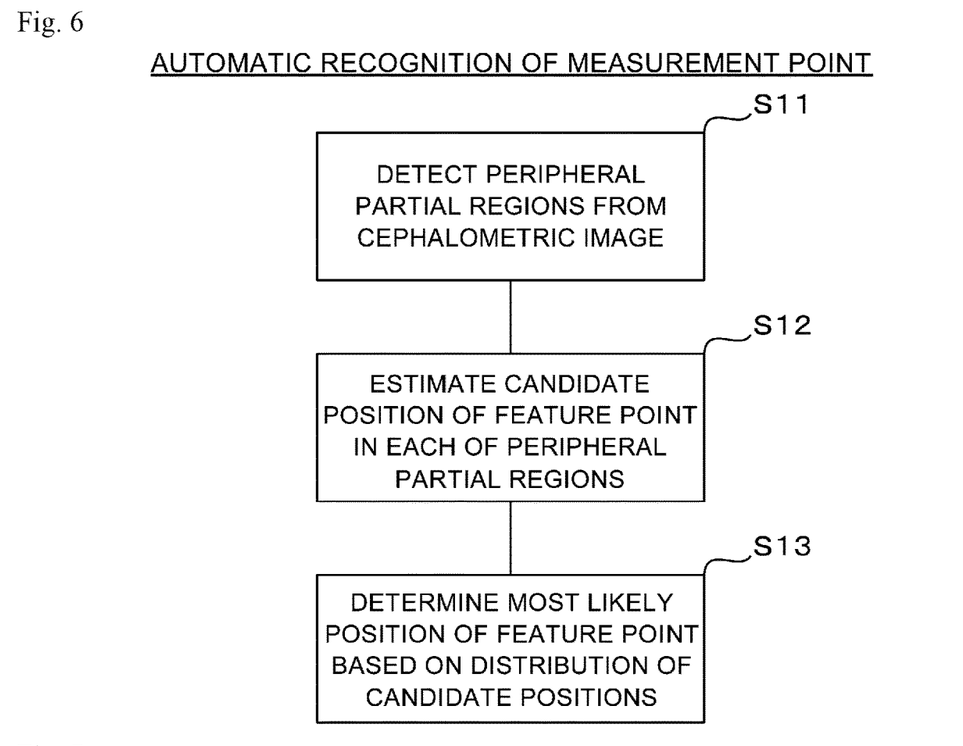
FIG. 6 is a flowchart illustrating a processing of automatically recognizing a measurement point according to an embodiment of the present invention.

FIG. 6 is a flowchart illustrating a processing of automatically recognizing a measurement point according to an embodiment of the present invention. This automatic recognition processing includes a step (S11) in which specific peripheral partial regions around a feature point of interest are detected from a cephalometric image acquired from a subject, a step (S12) in which a candidate position of the feature point is estimated in each of the peripheral partial regions detected, and a step (S13) in which the most likely position of the feature point in the cephalometric image is determined based on the distribution of the candidate positions estimated in the peripheral partial regions. The position of the feature point estimated by this automatic recognition method is recognized as the position of a measurement point in cephalometric image analysis (see FIG. 1), and is used in the quantitative measurement and assessment for orthodontic diagnosis.

Figure 7:
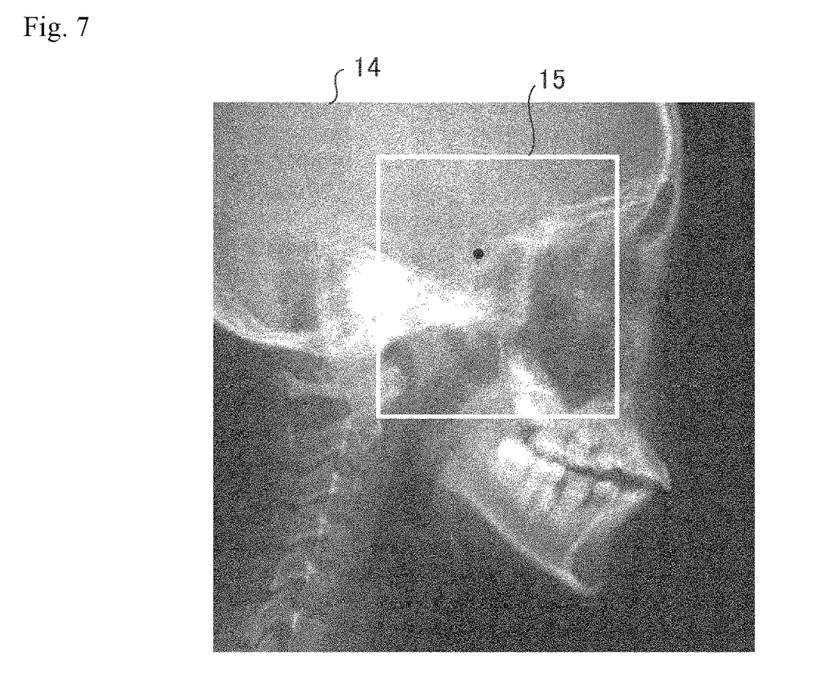
FIG. 7 is a view illustrating a cephalometric image and a large candidate region selected from the image.

First, in Step S11 in FIG. 6, a plurality of peripheral partial regions 31, 32, 33, 34, . . . is detected from a cephalometric image 14 of a subject input to the system, by an image recognition processing based on deep learning using, for example, a classification convolutional neural network model (hereinafter, written as "classification CNN model") illustrated in FIG. 9. The image that is input to the classification CNN model 13 may be the whole of a cephalometric image but is preferably a limited candidate region 15 including an anatomical feature point (for example, sella, nasion, etc.) of interest of recognition, as illustrated in FIG. 7. Here, this candidate region clipped from the whole image is referred to as a "large candidate region". Incidentally, the peripheral partial regions 31, 32, 33, 34 described hereinabove are smaller regions selected from a "large candidate region" and are therefore sometimes written as "small candidate regions".

When identifying a certain feature point from a cephalometric image by reading the radiograph, a specialist refers to a plurality of peripheral partial regions around the feature point. When the anatomical feature point to be identified is, for example, nasion (the foremost point of the frontonasal suture site), a specialist often follows procedures such as first looking for the frontal sinus, then looking for a transmitted image located anterior and inferior thereto (on the lower right on the image), and further considering the nasal morphology in search of a location which may serve as an anatomical suture site without any problems. Furthermore, the specialist considers again to confirm that he has not selected by mistake the eyelid line, and identifies the final foremost point of the nasal suture site. During this process, the specialist determines the position in a composite manner based on a plurality of anatomical features by, for example, recognizing an image portion that is as large as the frontal sinus on the upper left of the nasion on the image, then recognizing the morphology of the nose on the lower right of the nasion on the image, and further looking for the eyelid inferior to the nasion.

In the present specification, the term "peripheral partial region" indicates a specific image region around a feature point of interest that is selected by a specialist or other person who has anatomical knowledge, in order to identify the feature point in the cephalometric image. In a standardized cephalometric image, a plurality of peripheral partial regions around a certain feature point may be each specified in terms of pixel coordinate position and image size. The plurality of peripheral partial regions around a feature point have different image sizes from one another.

As used herein, the image size of a peripheral partial region is defined by the following equation (1).

$$\text{Image size} = \text{Number of pixels} \times \text{Resolution} \qquad \text{Eq. (1)}$$

Hereinbelow, an example will be described in which the large candidate region 15 illustrated in FIG. 7 is input (a large candidate region image 15D) to the present system and the position of sella as an exemplary feature point is automatically recognized by identifying sella based on a plurality of peripheral partial regions.

The present system includes an arithmetic processor and a database. The database stores, for example, data of a plurality of control images showing peripheral partial regions that have been predetermined with respect to a feature point of interest (such as, for example, sella), a classification CNN model 13 and/or 16 that is a deep learning model trained with the control images as teacher data, and a regression CNN model 10 that is a deep learning model trained to learn the position of the feature point in each of the peripheral partial regions.

The peripheral partial region detecting unit, the feature point position estimating unit and the most likely position determining unit described below are established by the arithmetic processor executing an arithmetic processing in accordance with a predetermined algorithm.

(Peripheral Partial Region Detecting Unit)

Figure 8:
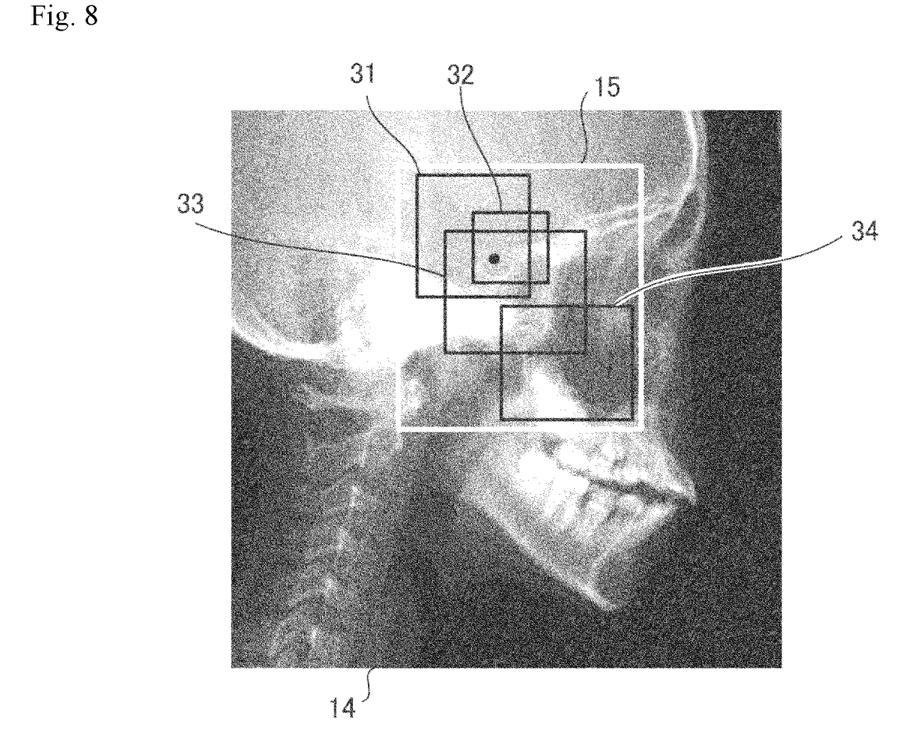
FIG. 8 is a view illustrating a plurality of peripheral partial regions referred to in the determination of the position of feature point sella in a cephalometric image.

Here, FIG. 8 is a view illustrating peripheral partial regions 31, 32, 33, 34, . . . that are referred to when identifying the position of the feature point sella in a cephalometric image 14 acquired from a subject. In Step S11 described hereinabove (see FIG. 6), the peripheral partial region detecting unit detects the peripheral partial regions 31, 32, 33, 34, . . . in the cephalometric image 14 by a deep learning processing based on a classification CNN model 13 that has been trained with teacher data, that is, control images, of a plurality of peripheral partial regions predetermined with respect to the feature point sella, and the peripheral partial region detecting unit clips peripheral partial region images (so-called "patches") 21, 22, 23, . . . corresponding to the respective peripheral partial regions.

Here, with reference to FIG. 9, an exemplary processing will be described which automatically detects a peripheral partial region 32 that matches a control image 52 that is a teacher image. First, a large candidate region image 15D including the feature point sella is selected from the cephalometric image 14 of the subject, and the data thereof is loaded into an input image buffer memory of the system. The large candidate region image 15D may be selected automatically or may be selected by a specialist or other person who actually operates, for example, moves a cursor while looking at the cephalometric image.

As already mentioned, the classification CNN model 13 has been trained in advance with control images 52 that are teacher images of peripheral partial regions 32 acquired in the past from many sample providers (including patients and healthy subjects). The present automatic recognition system creates, in a work memory, a scanning frame 32S having the same vertical and horizontal sizes as a control image 52 of a peripheral partial region 32 that is the target of detection. The region of this scanning frame 32S may be specified as, for example, [(Sx, Sy):(Sx+Lx, Sy+Ly)] where (Sx, Sy) are the start coordinate variables of the frame, and Lx and Ly are the image sizes in the X and Y axis directions of the peripheral partial region 32 that are added as offsets to the start coordinate variables, namely, (Sx+Lx, Sy+Ly) are the end coordinate variables.

Figure 9:
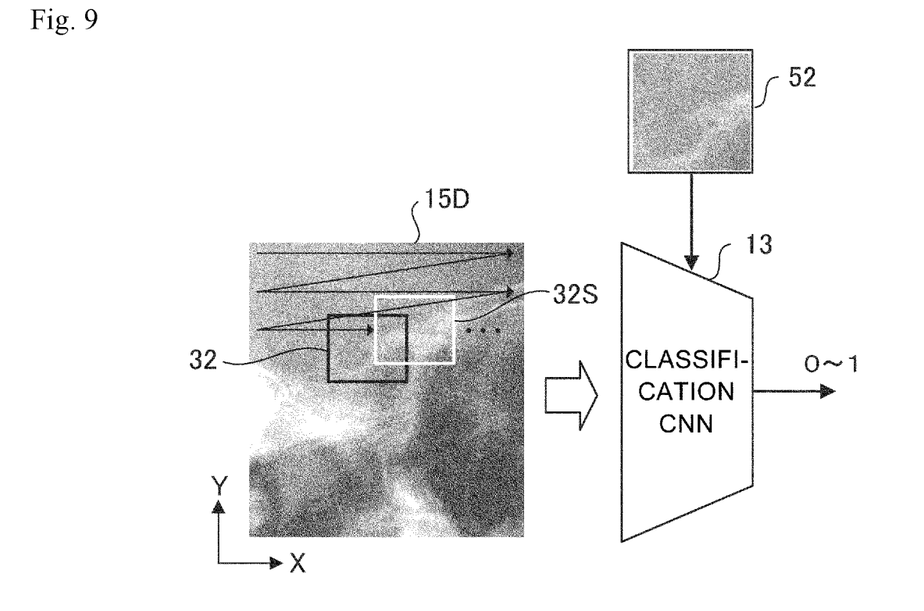
FIG. 9 is a view illustrating a system that detects a plurality of peripheral partial regions from a cephalometric image.

Thereafter, as illustrated in FIG. 9, the scanning frame 32S is scanned line by line on the large candidate region image 15D, and the classification CNN model 13 is applied to portions (scanned images) of the large candidate region image 15D that are sequentially scanned at respective scanning positions defined by the scanning frame 32S. The classification CNN model 13 compares the scanned image with the control image 52 of the peripheral partial region and determines the degree of matching (the degree of similarity) between the images. The peripheral partial region detecting unit detects a peripheral partial region 32 having the highest degree of matching with the control image 52 among all the regions scanned over the entirety of the large candidate region image 15D.

By adopting the above algorithm that uses a specific image size as a clue to finding a peripheral partial region matching a control image, the speed and accuracy of detecting a peripheral partial region may be enhanced.

The scanning within the scanning frame 32S is preferably performed in such a manner that units each consisting of several pixels are primarily scanned first to roughly narrow the target region in the large candidate region image 15D, and thereafter the narrowed target region is scanned pixel by pixel to detect a final peripheral partial region 32.

When identifying a feature point on a soft tissue, an experienced specialist may refer not only to peripheral parts around the feature point but also to skeletal structures of parts a little distant from the feature point (for example, a peripheral partial region 34 illustrated in FIG. 8). According to the present automatic recognition method, the pixel coordinate position of, for example, sella may be estimated relative to the peripheral partial region 34 that does not include the feature point sella.

Figure 10:
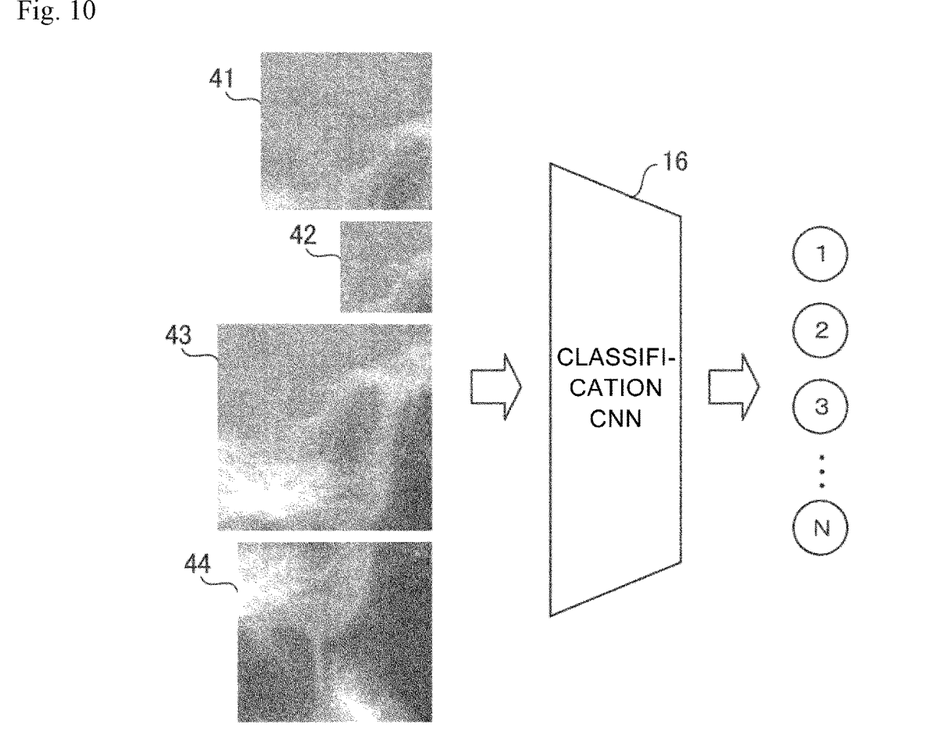
FIG. 10 is a view illustrating a system that classifies a plurality of segmented images to corresponding peripheral partial regions by applying a classification CNN model.

Alternatively, as illustrated in FIG. 10, a plurality of segmented images 41, 42, 43, 44 having various sizes may be selected from the large candidate region image 15D and the classification CNN model 16 may be applied to each of the images so as to classify the segmented images to the corresponding peripheral partial regions. In this case, a segmented image determined not to include the feature point, for example, the segmented image 44, may be excluded from the processing target.

(Feature Point Position Estimating Unit)

Figure 11:
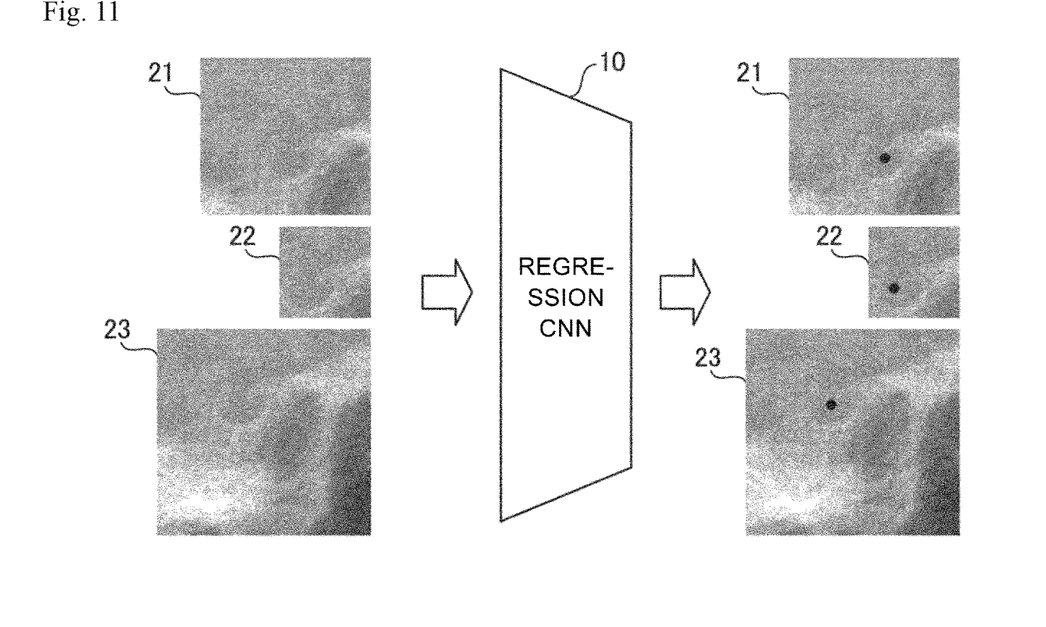
FIG. 11 is a view illustrating a system that applies a regression CNN model to a plurality of peripheral partial regions and estimates the position of a feature point in each peripheral partial region.
Figure 12:
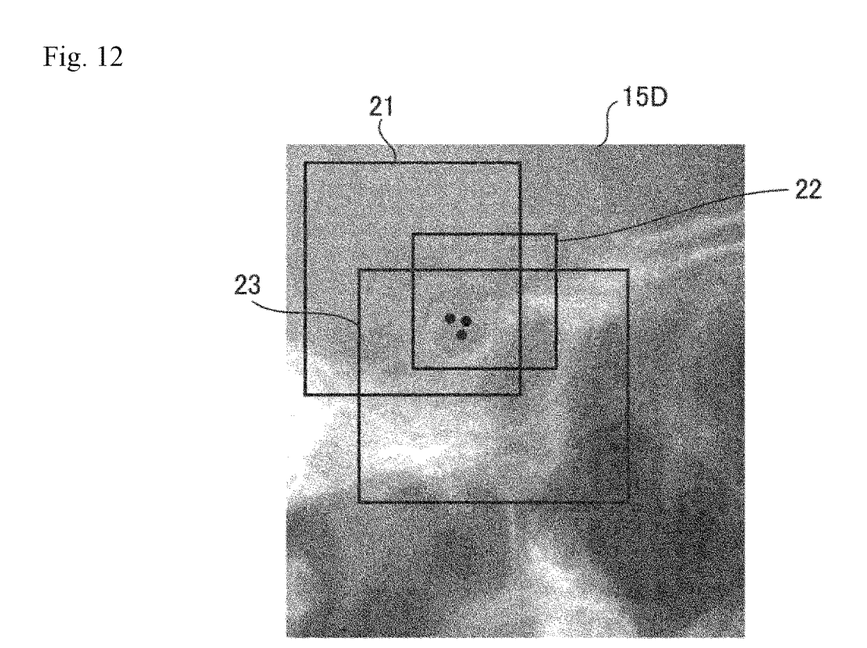
FIG. 12 is a view illustrating at the same time a plurality of candidate positions of feature point sella estimated in a large candidate region image.

Next, in Step S12 (FIG. 6), the candidate position of the feature point is estimated in each of the plurality of peripheral partial region images 21, 22, 23, . . . that have been clipped. In the present example, as illustrated in FIG. 11, the regression CNN 10 described hereinabove is applied to each of the peripheral partial region images 21, 22, 23, . . . to give relative pixel coordinate values of the candidate positions of the feature point sella that are indicated by black dots in the respective regions. To help the understanding of this, FIG. 12 illustrates an example of the large candidate region image 15D simultaneously showing a plurality of candidate positions estimated of the feature point sella.

(Most Likely Position Determining Unit)

Finally, in Step S13 (FIG. 6), the position of the feature point sella in the cephalometric image 14 (or the large candidate region image 15D) is determined by a maximum likelihood estimation processing based on the distribution of the candidate positions of the feature point sella estimated in the peripheral partial region images 21, 22, 23, . . . .

Figure 13:
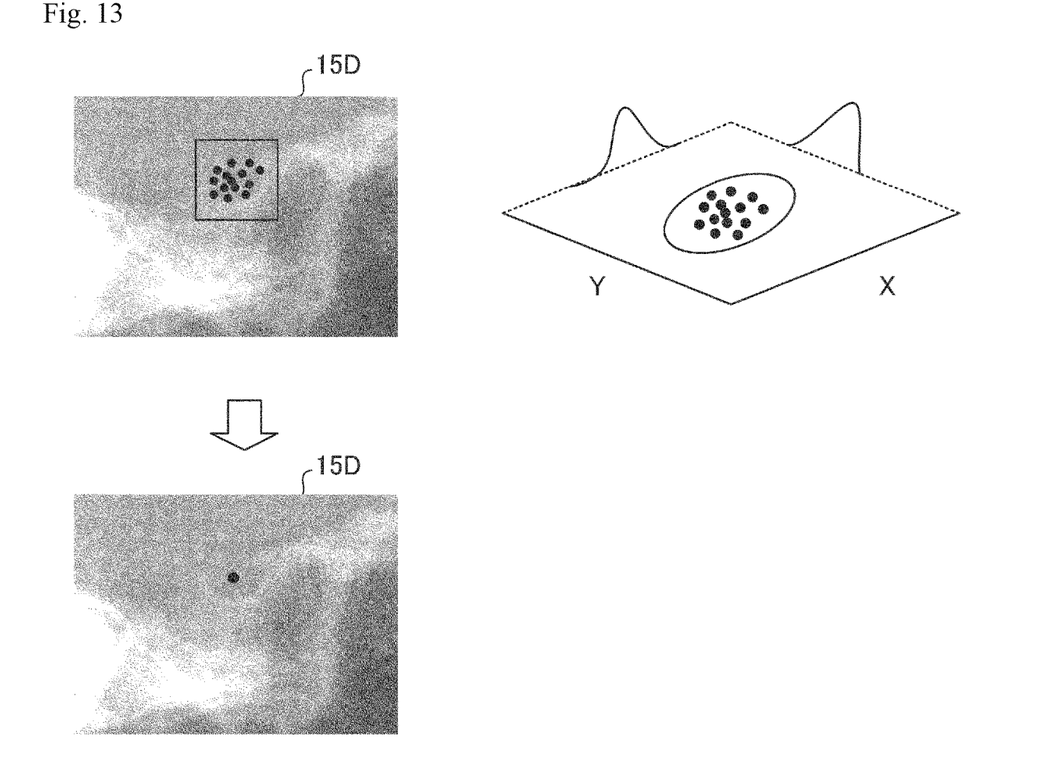
FIG. 13 is a view illustrating how the position of a feature point is determined based on density curves showing the distribution of a plurality of candidate positions.

For example, the position that is closer to the peak top of the distribution density curves than any other candidate positions indicated by black dots in FIG. 13 may be determined as the position of the feature point. Alternatively, the position of the peak top of the distribution density curves of the candidate positions may be determined as the position of the feature point.

Figure 14:
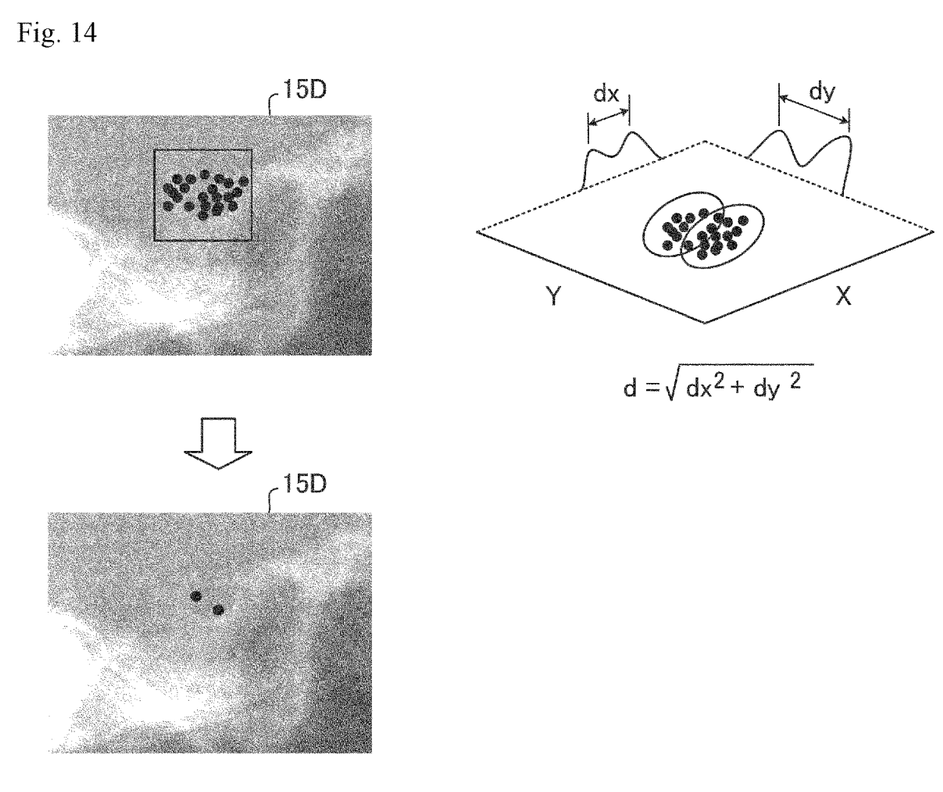
FIG. 14 is a view further illustrating how the positions of feature points are determined based on density curves showing the distribution of a plurality of candidate positions.

In other cases in which, for example, the distribution density of the candidate positions of the feature point shows at least two or more peaks as illustrated in FIG. 14, two or more feature points estimated based on the positions of these peaks may be determined as separate measurement points with respect to the feature point. In this case, the points may be determined as separate measurement points with the proviso that the distance between the two candidate positions is not less than a predetermined threshold value.

The most likely position determining unit includes regression CNN models 10 that are applied to the respective peripheral partial region images 21, 22, 23, . . . to estimate the position of, for example, the feature point sella. It is preferable that the regression CNN models 10 have been trained so that the error will be minimum between the candidate position of a feature point estimated from peripheral partial region images and the position of the feature point determined by a maximum likelihood estimation processing of cephalometric images 14 of subjects.

The accuracies in the estimation of candidate positions in Step S12 are variable depending on the peripheral partial region images based on which the estimation is made. Thus, the evaluation by the maximum likelihood estimation processing in Step S13 may be performed in such a manner that the results of the estimation of candidate positions are weighted according to the estimation accuracies. For example, the result of a candidate position estimated in the larger peripheral partial region image 23 may be weighted with a larger weighting coefficient than the result of a candidate position estimated in the smaller peripheral partial region image 22. Further, the tendency of error from the determination result in Step S13 may be learned, and the weighting coefficients may be controlled depending on the respective estimation accuracies.

Subsets each including some feature points may be automatically recognized by a parallel processing. For example, a parallel processing may be performed by training the system to learn separately:

Subset 1: {S, B, N, . . . }, and

Subset 2: {Po, Or, Me, . . . }.

Here, S, B, N, Po, Or, Me, . . . correspond to different anatomical feature points.

The feature points S, B, N, . . . that belong to Subset 1 may be each extracted based on the distribution in a plurality of peripheral partial regions as described hereinabove. The same applies to Po, Or, Me, . . . belonging to the other Subset 2.

A parallel processing of subsets that divide feature points in an ambiguous relationship with each other (such as being close or similar to each other) can concurrently attain a higher speed in the extraction of all feature points and an enhanced accuracy in the detection of all the positions.

In the method of the present embodiment in which feature points are divided into some subsets and are processed in parallel, the extraction processing may be performed as described hereinabove based on a learning model with respect to a plurality of peripheral partial regions around each of the feature points, or may be performed using a learning model with respect to candidate regions predetermined for each of the feature points.

REFERENCE SIGNS LIST

10 REGRESSION CNN MODEL (FOR ESTIMATING POSITION OF FEATURE POINT)
11 INPUT IMAGE
12 TEACHER IMAGE
13 CLASSIFICATION CNN MODEL (FOR DETECTING PERIPHERAL PARTIAL REGION)
14 CEPHALOMETRIC IMAGE OF SUBJECT
15 LARGE CANDIDATE REGION
15D LARGE CANDIDATE REGION IMAGE
16 CLASSIFICATION CNN MODEL (FOR CLASSIFYING PERIPHERAL PARTIAL REGIONS)
21, 22, 23 PERIPHERAL PARTIAL REGION IMAGES
31, 32, 33, 34 PERIPHERAL PARTIAL REGIONS
32S SCANNING FRAME
41, 42, 43, 44 SEGMENTED IMAGES
52 CONTROL IMAGE OF PERIPHERAL PARTIAL REGION
101 INPUT LAYER
102 HIDDEN LAYERS (DEEP LEARNING LAYERS)
103 OUTPUT LAYER
1021, 1022 NEURONS

The invention claimed is:

1. An automatic measurement point recognition method wherein a measurement point in a cephalometric image is automatically recognized with an arithmetic processor, the method comprising:
a step of detecting, from a cephalometric image acquired from a subject, a plurality of peripheral partial regions different from one another that have been predetermined with respect to a feature point of interest,
a step of estimating a candidate position of the feature point in each of the peripheral partial regions using a deep learning model trained to learn positions of the feature point in peripheral partial regions, and a step of determining a most likely estimated position of the feature point in the cephalometric image based on the distribution of the candidate positions estimated, and determining that the most likely estimated position is the position of the measurement point, wherein when the distribution density of the candidate positions shows at least two or more peaks and when any two candidate positions estimated as most likely positions from the tops of the respective peaks are distant from each other by a predetermined threshold value or a greater distance and, the step of determining the position of the feature point comprises a processing that determines that the two candidate positions are separate measurement points with respect to the feature point.

2. The automatic measurement point recognition method according to claim 1, wherein the peripheral partial regions have different image sizes from one another, and in the step of detecting the peripheral partial regions, the peripheral partial regions are each detected by comparison with a control image having the same size as the peripheral partial region.

3. The automatic measurement point recognition method according to claim 1, wherein in the step of determining the position of the feature point,
the candidate position closest to the peak top of the distribution density of the candidate positions is determined as the most likely estimated position of the feature point.

4. The automatic measurement point recognition method according to claim 1, wherein in the step of determining the position of the feature point,
the position of the peak top of the distribution density of the candidate positions is determined as the most likely estimated position of the feature point.

5. An automatic measurement point recognition system comprising an arithmetic processor capable of automatically recognizing a measurement point in a cephalometric image, and a database, wherein
the database stores:
information of a plurality of control images showing peripheral partial regions different from one another that have been predetermined with respect to a feature point of interest, and
a deep learning model trained to learn positions of the feature point in the peripheral partial regions, and
the arithmetic processor comprises:
a peripheral partial region detecting unit that detects, from a cephalometric image acquired from a subject, a plurality of peripheral partial regions that match the control images,
a feature point position estimating unit that estimates a candidate position of the feature point in each of the peripheral partial regions using the deep learning model, and
a most likely position determining unit that determines a most likely estimated position of the feature point in the cephalometric image based on the distribution of the candidate positions estimated, and determines that the most likely estimated position is the position of the measurement point, wherein when the distribution density of the candidate positions shows at least two or more peaks and when any two candidate positions estimated as most likely positions from the tops of the respective peaks are distant from each other by a predetermined threshold value or a greater distance, the most likely position determining unit determines that the two candidate positions are separate measurement points with respect to the feature point.

6. The automatic measurement point recognition system according to claim 5, wherein the peripheral partial regions have different image sizes from one another, and the peripheral partial region detecting unit detects each of the peripheral partial regions by comparison with the control image having the same size as the peripheral partial region.

7. The automatic measurement point recognition system according to claim 6, wherein the most likely position determining unit is configured to determine that the candidate position closest to the peak top of the distribution density of the candidate positions is the most likely estimated position of the feature point.

8. The automatic measurement point recognition system according to claim 6, wherein the most likely position determining unit is configured to determine that the position of the peak top of the distribution density of the candidate positions is the most likely estimated position of the feature point.

9. The automatic measurement point recognition method according to claim 2, wherein in the step of determining the position of the feature point,
the candidate position closest to the peak top of the distribution density of the candidate positions is determined as the most likely estimated position of the feature point.

10. The automatic measurement point recognition method according to claim 2, wherein in the step of determining the position of the feature point,
the position of the peak top of the distribution density of the candidate positions is determined as the most likely estimated position of the feature point.

11. The automatic measurement point recognition system according to claim 6, wherein the most likely position determining unit is configured to determine that the candidate position closest to the peak top of the distribution density of the candidate positions is the most likely estimated position of the feature point.

12. The automatic measurement point recognition system according to claim 6, wherein the most likely position determining unit is configured to determine that the position of the peak top of the distribution density of the candidate positions is the most likely estimated position of the feature point.

* * * * *